United States Patent [19]

Scanes et al.

[11] Patent Number: 5,407,681
[45] Date of Patent: Apr. 18, 1995

[54] INCREASING THE GROWTH OF TURKEYS USING IMPLANT OF 5-ALPHA-DIHYDROTESTOSTERONE

[75] Inventors: Colin G. Scanes, North Brunswick; Michael J. Fennel, Jr., Wall, both of N.J.

[73] Assignee: Rutgers, The State University of New Jersey, New Brunswick, N.J.

[21] Appl. No.: 52,208

[22] Filed: Apr. 21, 1993

Related U.S. Application Data

[63] Continuation-in-part of Ser. No. 905,192, Jun. 26, 1992, Pat. No. 5,208,032, which is a continuation of Ser. No. 219,710, Jul. 15, 1988, abandoned.

[51] Int. Cl.⁶ .............................................. A61F 13/00
[52] U.S. Cl. ..................................... 424/422; 424/423; 424/424; 424/425; 424/426; 424/433; 424/451; 424/486; 514/178; 514/772.3
[58] Field of Search ................................ 424/422–426, 424/433, 486, 451; 514/178, 772.3

[56] References Cited

U.S. PATENT DOCUMENTS 5,208,032  5/1993  Scanes et al. ...................... 424/422

*Primary Examiner*—Thurman K. Page
*Assistant Examiner*—Jyothsna Venkat
*Attorney, Agent, or Firm*—Leroy G. Sinn

[57] ABSTRACT

Provided by the invention are methods and compositions for increasing the growth rate and feed efficiency of turkeys by administration of an effective amount of 5-alpha-dihydrotestosterone or biocompatible derivatives such as alkanoic acid ester derivatives, as an implant.

8 Claims, No Drawings

INCREASING THE GROWTH OF TURKEYS USING IMPLANT OF 5-ALPHA-DIHYDROTESTOSTERONE

CROSS-REFERENCE TO RELATED APPLICATIONS

This application is a continuation-in-part application of U.S. application Ser. No. 07/905,192, filed Jun. 26, 1992, now U.S. Pat. No. 5,208,032 which is a continuing application of U.S. application Ser. No. 07/219,710, filed Jul. 15, 1988 (now abandoned).

TECHNICAL FIELD

This invention relates to a method of increasing the growth rate and feed efficiency of turkeys as well as increasing the muscle mass but reducing the relative body fat. Also provided are compositions or devices which are adapted to provide systemic absorption of the natural compound 5-alpha-dihydrotestosterone, biocompatible derivatives thereof or combinations thereof to promote said growth.

BACKGROUND ART

It is desired in the turkey producing art to provide increased rate of growth and efficiency of feed utilization. Additionally, it is desired at the same time to provide with the increased growth an increase in muscle mass such as breast weight but preferable also a decrease in percentage of fat mass.

Such a process would not only increase the profitability to the grower of turkeys but would also provide a highly desired increase in edible muscle mass having a lower relative amount of fat mass. It is widely desired to have protein source such as turkey meat with a reduced fat content. It is well known that excessive fat in the diet should be avoided to provide better weight control, health and life expectancy.

Also desired are compositions or devices adapted to provide a slow, continuous release of the active agent for systemic absorption by the turkey.

SUMMARY OF INVENTION

It has been found that administration of an effective amount of 19-nortestosterone, an intermediate in steroid synthesis, provides an increase in growth rate and feed efficiency in turkeys as well as providing an increase in muscle mass along with a lower relative amount of fat mass in the turkey carcass. It has been found that administration of at least about 5 mg in the form of a 21-day constant release subcutaneous implant is suitable. A presently preferred dosage in the form of such a subcutaneous implant is at least about 20 mg, with a dosage of about 50 mg being highly suitable. It has been found suitable to administer the 19-nortestosterone subcutaneously, for example, below the ear of the turkey, using conventional implanting devices. The dosage can be administered in the form of an implant device which releases the 19-nortestosterone slowly in a desired constant rate, over a period of time such a about 21 days or more. Desirably, the implant can be in the form of a capsule enveloping the 19-nortestosterone which provides the desired slow, constant release or in the form of a polymer mass pellet having encapsulated or dispersed therein 19-nortestosterone so as to permit by diffusion or slow dissolution release subcutaneously and subsequent systemic absorption. It has been found suitably to use silicone rubber as a polymeric encapsulating material.

Other related compounds can be used instead of or in combination with 19-nortestosterone. Included in such related compounds are biocompatible derivatives of 19-nortestosterone which are effective in the methods of this invention, such as active esters or the like. Also, instead of or in combination with 19-nortestosterone, 5-alpha-dihydrotestosterone can be used in carrying out the procedures described herein to make the compositions and performing the processes described herein. Also biocompatible derivatives of 5-alpha-dihydrotestosterone, such as its esters, which are effective in the methods of the invention can be used alone or in combination with 5-alpha-dihydrotestosterone in carrying out the procedures of the invention described herein to provide unexpectedly beneficial results. Reference in this regard is made to parent patent application Ser. No. 07/219,710, filed Jul. 15, 1988. An amount of about 5 to about 65 percent, desirably about 10 to about 60 percent by weight of 19-nortestosterone or biocompatible derivatives thereof which are effective in carrying out the methods of this invention, can be used to replace in the compositions of this invention, a corresponding amount of 5-dihydrotestosterone or biocompatible derivatives thereof which are useful in making the compositions of this invention.

DETAILED DESCRIPTION OF THE INVENTION AND THE PREFERRED EMBODIMENTS

The growth promoting agent 19-nortestosterone is a known chemical. It is a natural compound which can be produced as an intermediate in steroid biosynthesis. It has the following chemical structure compared with the chemical structures of testosterone and 5-alpha-dihydrotestosterone:

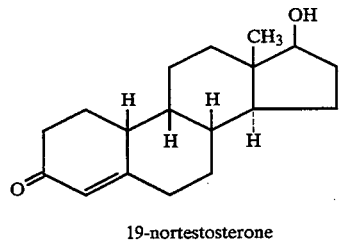

19-nortestosterone
(Nandrolone)

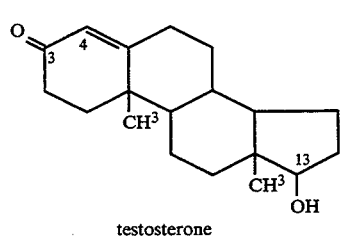

testosterone

-continued

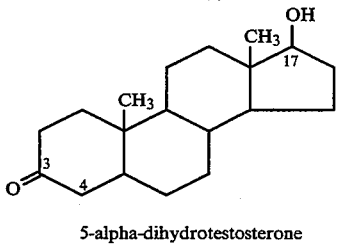

5-alpha-dihydrotestosterone

The compound 19-nortestosterone is administered to the turkeys so as to be absorbed systemically. A suitable manner of administration is to insert subcutaneously a solid dosage form. The solid dosage form is referred to as an implant. The implant can be inserted in any suitable subcutaneous portion of the turkey. A suitable place has been found to be the conventional location back of the neck and behind the ears.

The implant can be in any biocompatible geometric form, such as a cylinder, tablet, sphere or the like. It is desirable that the implant be free of sharp edges or points. Implants with such sharp edges or points can fail to be bioacceptable to the turkey.

It has been found suitable to use a cylindrical form. A functional form has been made using a bioacceptable, medical grade polysiloxane rubber tubing sold under the trademark Silastic. A suitable I.D. has been found to be 1.57 cm. The 19-nortestosterone in the form of small crystals can be filled into the tubing to make intimate contact with the internal wall surfaces of the tubing. The ends of the tubing may be closed in any suitable manner, such as by inserting wooden dowel plugs at each end. Any suitable length and diameter can be used. It has been found suitable to use a polysiloxane rubber tubing having an inside diameter of 1.57 cm and a length of 1 cm or longer as needed. For the sale of evaluation it has been found suitable to close the ends of the tubing by inserting at each end suitable wood dowel plugs. The 19-nortestosterone in the form of small crystals can be placed inside the tubing in making the implants. The crystals can also be suspended in a bioacceptable extending agent suitable to permit proper diffusion through the walls of the tubing. For purposes of use as a control, an implant can be formed by filling a section of the tubing with cholesterol or other suitable agent inactive for growth promotion. The implant can be in the form of a solid pellet, disc or sphere. It has been found suitable to disperse the 19-nortestosterone in a suitable polymer and form a pellet thereof, following technique known in the art.

Alternately, an implant can be made using an insert core as a base for coating thereon a mixture of 19-nortestosterone and an extending agent such as a medical grade polymethylsiloxane rubber. A suitable coating solvent can be used. Also, a crosslinking agent can be included to provide an insoluble coating comprising 19-nortestosterone dispersed in the polymethylsiloxane rubber coating. Conventional crosslinking agent for polymethylsiloxane can be used, such as a usual amount of stannous octanoate.

The amount or concentration of the 19-nortestosterone will be adjusted to provide the desired daily dosages diffusing from the subcutaneous implants. The coating can alternatively be made by using a suitable polymer with a slow dissolution rate permitting a regulated release of daily dosages. In such an instance, a core can be employed which is biosoluble. In such implants, the exposed biosoluble and biocompatible core will dissolve and disappear.

Reference is made for assistance in making suitable implants to U.S. Pat. Nos. 2,413,419; 2,895,875; 3,428,729; 3,830,907; 3,857,932; 4,096,239; and 4,191,741. These patents are incorporated herein to extent useful for making suitable implants.

Administration of 19-nortestosterone be made in other suitable ways known or developed by the art in order to provide effective systemic administration of 19-nortestosterone in accordance with this invention.

The 19-nortestosterone can be administered in the form of biocompatible derivatives which provide the 19-nortestosterone activity as provided by this invention. Ordinarily, such activity of a suitable derivative will result when the derivative such as an ester will be bioconverted to the parent compound 19-nortestosterone after subcutaneous or other suitable administration to the turkey in which growth promotion or increased feed efficiency is desired in accordance with the invention described herein. Such biocompatible derivatives can be selected from carboxylic acid derivatives, such as alkanoic acid derivatives, which can be selected from the decanoate, p-hexyloxyphenylpropionate, phenpropionate, propionate and the like.

A suitable amount of 19-nortestosterone to be administered to a turkey has been found to be about 5 mg to about 50 mg or more administered as a subcutaneous implant designed to release 19-nortestosterone at an effective and constant rate over a 21-day period. Such an implant having about 50 mg has been found to be an effective amount. The amount of 19-nortestosterone incorporated can be varied and yet provide effective growth promotion under this invention, depending on growth rate desired, the turkeys treated, the implants or other dosage forms used and other factors.

The administration to the turkey to provide the described growth promotion or increased feed efficiency can be made at any suitable age. It has been found suitable to administer to turkeys, for example, appropriate implants can be inserted at about 3 to about 8 weeks of age, desirably up to 7 weeks of age. Supplemental administration of an implant can be made to the turkeys as indicated or desired to obtain optimal growth promotion or increased feed efficiency, depending 19-nortestosterone upon the nature of the implants used and other factors.

A suitable turkey variety can be used which provides effective response in the practice of this invention. It has been found, for example, that large white strains of turkeys have been suitable, as described herein under the Examples. The turkeys used in the invention can be males, castrated males or females.

In carrying out the invention, good growing practices are to be employed as are known to those familiar with growing turkeys for human consumption. Conventional balanced feeds can be used, which are available commercially. The feed can be made available on an ad libitum basis. For example, Agway Game and Turkey Starter Crumbles commercial feed has been found to be satisfactory.

As stated above, it has been observed that turkeys grown by following the invention described herein provide certain advantages, including increased growth rate with little or no skeletal growth over controls, increased weight of edible muscle mass, comparable decrease in relative fat mass, and increased feed efficiency.

Appropriate analytical and test procedures for monitoring and carrying out the invention are described in the Examples of the specification. For example, insertion of suitable implants can be made using devices and techniques well known to those skilled in the turkey growing art. Likewise, if desired, male turkeys can be castrated also using devices and techniques well known to those skilled in the art.

The data of the Examples show that results in turkeys by administration of 19-nortestosterone in accordance with the methods of this invention (Table IV and Table V) show unexpectedly superior advantages over corresponding administration of testosterone to turkeys (Table IV and Table V) and unexpectedly superior results over corresponding administration of 19-nortestosterone to chickens (Table III). Instead of 19-nortestosterone, 5-alpha-dihydrotestosterone can be used in carrying out the above described procedures to provide unexpectedly beneficial results. It is a natural compound. The following examples are in illustration of the invention and are not intended to be limiting. Full citations of references cited in the Examples appear at the end of the Examples.

EXAMPLE 1

A. Experimentation with Chickens

The single comb White Leghorn strain (Dekalb XL) of chicken (Avian Services, Frenchtown, NJ) was used in all studies. Chicks were obtained on the day following hatch and were then maintained in a well ventilated, temperature-and humidity-controlled animal room. Chicks were housed in temperature-controlled (access to small brood chambers—32° to 35° C.), wire-floored, 5-tier brooder batteries (measuring 0.74 W×1.55 L×0.27 H m per tier) until termination of respective studies. A 12 hour light:12 hour dark photoperiod was maintained at all times within the animal room. Feed and water were available ad libitum, with a standard commercial diet (Agway; Bordentown, N.J.), chick starter mash, fed to chicks 1 to 42 days of age, and then from 43 to 84 days, grower mash was provided (manufacturer statement on ration compositions are shown in Table 2).

Excluding Study II, chicks were either castrated (Quigley, 1967) or sham-operated at 13 days of age. Prior to castration, cockerels were deprived of feed and water for 24 hours in order that the intestines may become empty and thus permit better vision into the body cavity and accessibility to testes. Birds were restrained by fastening the wings and legs with leather straps so that sufficient tension was applied to hold the bird well stretched out in a lateral recumbency (on its left side). Next, an approximate

TABLE 2

THE GUARANTEED ANALYSIS OF AGWAY* COUNTRY GAME AND TURKEY STARTER CRUMBLES, AGWAY COUNTRY CHICK STARTER MASH AND AGWAY COUNTRY CHICKEN GROWER MASH.

| | Crude Protein (min. %) | Crude Fat (min. %) | Crude Fiber (max. %) | Metacolizable Energy (Kcal/kg) |
|---|---|---|---|---|
| Game & Turkey Starter | 28.00 | 3.00 | 4.00 | 2904–3014 |
| Chick Starter | 18.00 | 3.00 | 4.00 | 2915–3025 |

TABLE 2-continued

THE GUARANTEED ANALYSIS OF AGWAY* COUNTRY GAME AND TURKEY STARTER CRUMBLES, AGWAY COUNTRY CHICK STARTER MASH AND AGWAY COUNTRY CHICKEN GROWER MASH.

| | Crude Protein (min. %) | Crude Fat (min. %) | Crude Fiber (max. %) | Metacolizable Energy (Kcal/kg) |
|---|---|---|---|---|
| Chicken Grower | 14.50 | 3.50 | 4.00 | 2992–3080 |

*Agway Feed Company, Bordertown, New Jersey 1 inch incision was made midway between the last two ribs and a small rib spreader inserted to hold the ribs about ½ inch apart. Forceps were used to remove both testicles, with the lower or left testicle removed first. The forceps were carefully worked over the testicle and so manipulated as to enclose the entire organ. It was then drawn out with a slight twisting motion. At this step, care was taken not to rupture any of the primary blood vessels. When the rib spreader was removed, and the tension on the bird released (i.e., leg and wing straps removed), the skin and thigh muscles slipped back over the incision thus affording a natural protection. No special care was necessary for surgically manipulated birds other than to puncture "air pockets" which developed under the skin due to air escaping from within the abdominal cavity before the incision between the ribs was healed.

In all studies, chicks were rank-ordered by weight, wing-banded and distributed into treatment groups of equal body weights at 14 days of age. Excluding Study I, e.g., in which male, female and castrate male comparisons were made, all control groups were implanted with 1.0-cm length cholesterol-filled Silastic polysiloxane implants (i.e., steroid surface exposure of 1.0-cm; actual length was 2.0-cm with ½ cm wood dowel plugs placed at each end of implant). The remaining treatment groups consisted of chicks (male, female or castrated male) implanted with either testosterone-, 5-alpha-DHT-, 5-beta-DHT-, estradiol-17-beta-, or 19-nortestosterone-filled Silastic polysiloxane implants ("DHT" is used herein at times as an abbreviation for dihydrotestosterone) with steroid surface exposures of either 0.3, 1.0 or 3.0 cm in length. Steroid implants were prepared by manually packing respective crystalline steroids (Steraloids; Wilton, N.H.) into Silastic Medical Grade tubing (1.57 mm i.d.; Dow Corning) (Smith et al., 1977). The amounts of steroid contained in the implants were as follows (mean±SEM of 20 randomly chosen implants, 5 for each steroid): 2.6±0.2 mg (0.3-cm), 8.9±0.4 mg (1.0-cm), and 29.2±0.7 mg (3.0-cm). At the time of group assignment, implants were placed in the subcutaneous (S.C.) layer of skin behind the neck. Supplemental steroid implants (containing doses of steroids equivalent to those of the initial implants) were implanted at 6 and 10 weeks of age, without removal of prior implants, to ensure adequate androgen replacement with increasing growth. Cage floors and fecal collection trays were checked for 2 consecutive days following each implantation session to ensure completeness of procedure. This system of steroid delivery has been previously demonstrated to maintain physiological concentrations of androgens in the castrate White Leghorn chicken (Johnson and Rendano, 1984). An outline of individual studies along with experimental treatments (i.e., type and dose of steroid) and number of birds per treatment group is given in Table 3.

Body weight and shank-toe length (King, 1969; combined length of metatarsus and longest toe which is an estimate of bone growth) were measured at weekly (or biweekly in Study I) intervals from the beginning through the end of each study. At the termination of studies I (12 weeks of age), III (12 weeks of age), IV (12 weeks of age) and V (6 weeks of age), several organs were excised and immediately weighed at necropsy. Relative tissue weights (percent of final body

EXAMPLE 2

Study I Comparison of Growth on Treated Male Turkeys

At 7 weeks of age, forty-nine male turkeys were rank ordered by weight and assigned to 7 treatment groups (8 birds/group) of equal mean weights. Within treatment groups, two birds were individually caged (layer cages measuring 0.31 W×0.46 L×0.53 H meters/cage)

TABLE 3

PROTOCOL OF STEROID TREATMENTS IN CHICKEN EXPERIMENTS II, III, IV, AND V.

| Experiment | Control | Treatments | | | | | |
|---|---|---|---|---|---|---|---|
| II a. (n = 10/group) | Intact Male (1.0-cm) Cholesterol | Intact Male (1.0-cm) Testosterone | Intact Male (1.0-cm) 5-alpha-DHT | Intact Male (1.0-cm) 5-beta-DHT | Intact Male (1.0-cm) $E_2$ | | |
| b. (n = 10/group) | Intact Female (1.0-cm) Cholesterol | Intact Female (1.0-cm) Testosterone | Intact Female (1.0-cm) 5-alpha-DHT | Intact Female (1.0-cm) 5-beta-DHT | Intact Female (1.0-cm) $E_2$ | | |
| III (n = 15/group) | Castrate Male (1.0-cm) Cholesterol | Castrate Male (1.0-cm) Testosterone | Castrate Male (1.0-cm) 5-alpha-DHT | Intact Male (1.0-cm) Cholesterol | | | |
| IV (n = 15/group) | Castrate Male (1.0-cm) Cholesterol | Castrate Male (0.3-cm) Testosterone | Castrate Male (1.0-cm) Testosterone | Castrate Male (3.0-cm) Testosterone | Castrate Male (0.3-cm) 5-alpha-DHT | Castrate Male (1.0-cm) 5-alpha-DHT | Castrate Male (3.0-cm) 5-alpha-DHT |
| V (n = 15/group) | Castrate Male (1.0-cm) Cholesterol | Castrate Male (0.3-cm) 19-N | Castrate Male (1.0-cm) 19-N | Castrate Male (3.0-cm) 19-N | Castrate Male (0.3-cm) 5-alpha-DHT | | |

Birds were removed from an experimental group if they died or developed postratal abnormalities.
[a]Steroid treatment entailed the S.C. implantation of silatic implants at 2, 6 and 10 weeks of age.
5-alpha-DHT = 5-alpha-dihydrotestosterone
5-beta-DHT = 5-beta-dihydrotestosterone
$E_2$ = Estradiol 17-beta
19-N = 19-Nortestosterone weight) and body weight minus [comb plus wattle weights] (i.e., final adjusted body weight) were also calculated. Excluding Study I, biweekly blood samples were obtained by venipuncture of the wing vein from the same individual birds for respective treatments. After centrifugation of whole blood, plasma was removed and stored at −20° C. until hormone assays were performed.

B. Experimentation with Turkeys

The same large white strain of turkey (received 1 day posthatching from Nicholas Breeding Farms, Calif.) was used in all studies. Poults were reared in deep litter brooder pens from 1 day posthatch and exposed to constant light until initiation of Studies I and III or through completion in the case of Study II. Studies I and III were conducted in an environmentally controlled room (photoperiod 12L:12D) with birds housed individually in wire-floored layer cages (space dimensions of 0.31 W×0.46 L×0.53 H meters per cage). Water and feed (Agway Game and Turkey Starter Crumbles) was available at all times. Turkeys were rank ordered by weight and distributed into treatment groups of equal mean body weights at the start of each Study (I, II and III).

Body weight determinations were made at the second and final week of each study, and several organs and tissues were excised and immediately weighed at the time of necropsy. Final shank-toe length, as an indicator of skeletal growth, was also determined. Birds were sacrificed via exanguination by laceration of the jugular vein. Specific details on the experimental design and conduct of each turkey study will follow.

side by side on one of three tiers (5 cages/tier and 3 tiers/rack). The middle cage was left empty, and that section of feeder (one continuous feeder for all five cages per tier) covered, hence, allowing feed consumption for each set of birds to be determined. Individual treatment units (or bird sets) were randomized (planned) into cages among tiers and racks to eliminate any rack (5) or tier (3 vertical) effects within the room. Hence, birds set on different treatments were placed into cage sets such that each tier (3 tiers per rack) contained two different treatment units (i.e., Rack 1—top tier contained treatment unit 1 on left side and treatment unit 2 on right side, while the middle tier contained treatment unit 3 on the left side and treatment unit 4 on the right side with the lowers tier containing treatment unit 5 on the left side and treatment unit 6 on the right side, etc. throughout remaining tiers and racks in room).

Treatments entailed the subcutaneous implantation (between the shoulders) of testosterone, 5-alpha-DHT or 19-nortestosterone as either a 50-mg pellet (Innovative Research of America, Rockville, Md.) or as a 5.0-cm crystalline filled Silastic polysiloxane implant [i.e., comparable implant size per body weight as the low (0.3-cm) dose in chickens]. Group 1 control males were implanted with a 50-mg compressed (methylcellulose/-lactose) placebo pellet. The remaining 6 treatment groups were as follows: Group 2, 50-mg testosterone pellet; Group 3, 50-mg 5-alpha-DHT pellet; Group 4, 50-mg 19-nortestosterone pellet; Group 5, 5.0-cm testosterone Silastic polysiloxane capsule; Group 6, 5-cm 5-alpha-DHT Silastic polysiloxane capsule and Group 7, 5.0-cm 19-nortestosterone Silastic polysiloxane capsule. Excluding feed efficiency, data means for all parameters were compared between treatments using individual birds as replicates (n=8). Data means for feed efficiency were compared between treatments using sets of birds as replicates (n=4).

EXAMPLE 3

Study II Comparison of Growth in Treated Female Turkeys

At 6 weeks of age, seventy-seven female turkeys were rank ordered by weight and assigned to 7 treatment groups (11 birds per group) of equal mean weights. Within treatment groups, birds were further allotted to deep-litter pens (3.66×4.27 m) containing 4 subdivisions (0.91×1.22 m), with 3 birds per subdivision except for the last which contained 2. Individual treatment units (or pen subdivisions) were randomized (planned) among pens within the building, such that each pen contained 4 different treatment units (3 or 2 birds each). Feed consumption for each treatment unit was measured; thus, 4 replicates per treatment for feed consumption and feed/gain ratios (or feed efficiency) were calculated.

Treatments entailed the subcutaneous implantation (between the shoulders) of testosterone, 5-alpha-DHT or 19-nortestosterone as either a low (5-mg) or high (50-mg) dose pellet (Innovative Research of America, Rockville, Md.). Implants were specially constructed (steroid compressed into a methylcellulose/lactose pellet) to release respective steroids at a constant rate over a 21 day period (manufacturer statement). In support, a recent report by Satyaswaroop et al. (1984) on mice, found Innovative Research 17 beta-estradiol pellets to have excellent 21-day continued release characteristics (i.e., maintained blood levels of 20–30 ng/ml for 21 days). Group 1 controls were composed of females implanted with a 50-mg placebo pellet. The remaining 6 female treatment groups were as follows: Group 2, testosterone (5-mg); Group 3, 5-alpha-DHT (5-mg); Group 4, 19-nortestosterone (5-mg); Group 5, testosterone (50-mg); Group 6, 5-alpha-DHT (50-mg) and Group 7, 19-nortestosterone (50-mg). Excluding feed efficiency, data means for all other parameters were compared between treatments using individual birds as replicates (n=11). Data means for feed consumption and feed efficiency were compared between treatments using pen subdivisions (3 or 2 birds/subdivision) as replicates (n=8).

EXAMPLE 4

Study III Growth Comparison in Male, Female and Castrate Male Turkeys Versus Castrate Male Turkeys Implanted with 19-Nortestosterone Male and female turkeys were either sham-operated or castrated (Quigley, 1962) at 4 weeks of age in the same manner as previously described for chickens. However, due to the small size and extremely viscous nature of the turkey testicle at 2 weeks of age, birds were castrated at 4 weeks of age. Even at this age, special care was required to ensure completeness of procedure (i.e., testis still did not have the same consistency or firmness as compared to that of the chicken testis). This was important since when a portion of the testicle is left behind or dropped back inside the body cavity after having been torn loose, the bird will become what is called in the poultry industry, a "slip". Due to hypertrophy of the testicular remnant and hence, secretion of the male sex hormones, "slips" will usually develop all the external appearances of a normal male (Card et al., 1972).

Pre- (4 weeks) and post-surgically (1 week), birds were floor-reared together on pine shavings. At 5 weeks of age, birds were transferred to individual layer cages (dimensions as in Study I) in an environmentally controlled animal room. One week later (6 weeks of age), birds were assigned to 4 groups (9 birds/group). Group 1 was composed of intact males (sham-operated); Group 2, intact females (shamoperated); Group 3, castrated males implanted that same day with cholesterol-filled Silastic polysiloxane capsules (5.0-cm); and Group 4, castrated males implanted that same day with 19-nortestosterone-filled Silastic polysiloxane capsules (5.0-cm). Castrated males were rank ordered by weight prior to group assignment. Male and female groups were composed of birds which had the intermediate body weights from a pool of 15 birds for each sex. Birds were randomized (planned) into cages among tiers (5 cages per tier) and racks, similar to that of Study I, in order to eliminate any rack (4) or tier (3 vertical) effects within the room. Birds served as individual treatment units for all parameters measured including feed consumption (i.e., supplied with individual box-type feeders) and were placed into every other cage starting on the top tier in rack 1. Hence, treatment units (i.e., individual birds in this case) were placed into cages such that each tier (3 tiers per rack) contained 3 different treatment units.

Hormone Assays

Radioimmunoassay Procedure for Testosterone

Plasma concentrations of testosterone were assayed using component kits from Immuchem Corporation (Carson, Calif.) in which charcoal-stripped chicken plasma (free of testosterone) was used to make up the standards. The antibody is covalently bound to the inner surface of each polypropylene tube (testosterone-19-carboxymethylether-BSA was the antigen used to generate the antiserum in rabbits). To these tubes (at room temperature), a 50 microliter volume of either standard or unknown plasma as added directly without extraction. Following this, a 1000-microliter volume (~40,000 cmp) of $^{125}$I-testosterone (purified by HPLC and radio-iodinated at position 19; Immuchem Corp.) in phosphosaline buffer-gelatin (pH 7.0) was added and the mixture was vortex mixed briefly. After a 2 hour incubation at room temperature, tubes were placed into styrofoam holding racks and the supernatant decanted onto tin trays lined with newspapers. Residual supernatant left on inside walls of tubes was removed by everting styrofoam holding racks and impacting them onto dry absorbent paper towels. At this point, the assay tubes, with their wall bound antibody-antigen complexes, were counted on a Beckman 5500 gamma counter to determine the radioactivity ($^{125}$I-testosterone) which was antibody-bound. The plasma concentrations of testosterone in unknown samples were determine based on the standards (from 0.10–10ng/ml) in charcoal-stripped chicken plasma included with each assay.

The Immuchem testosterone antiserum cross-reacts 100% with testosterone, 7.8% with 5-alpha-DHT, 0.56% with 4-adrosten-3,17-dione, and less than 0.01% with 5-alpha-androstane-3-alpha,17-beta-diol and estrogens (manufacturer statement). Sensitivity [i.e., lowest concentration of hormone which gave CPM significantly different from CPM given by the $B_o$ dose (has only labeled hormone and antibody)] of the assay ranged between 18 and 22 pg/ml, while the mean within-assay coefficient of variation (CV) for low (29 pg/ml for plasma pooled from 3 adult castrated male White Leghorn chickens) and high (2.68 ng/ml for plasma pooled from 3 adult intact male White Leghorn chickens) plasma pools (n=5) was less than 8%. The mean between-assay CV for low and high plasma pools was less than 11.0% (n=5). A typical standard curve (n=5) using 1.95 pg to 500 pg testosterone showed 50 percent inhibition of binding with 78.8±9.6 pg/tube (CV=12.2%). Twenty and 80 percent inhibition of binding were achieved with 15.8±1.7 pg/tube (CV=10.8%) and 462.5±1.5 pg/tube (CV=4.6%), respectively.

Radioimmunoassay Procedure for 5-alpha-DHT

The following will briefly outline the procedure used for determination of plasma concentration of 5-alpha-DHT. The 5-alpha-DHT anti-serum (Ford's-F/1) was kindly provided by Dr. Alan L. Johnson, Rutgers University, New Brunswick, N.J. This antibody reacted 100% to 5-alpha-DHT, 7.9% to testosterone and 11.4% to androstenedione. The antibody was diluted to 1:20,000 in PBSG and stored at 4° C. until added to assay that same day. This dilution resulted in approximately 35% binding.

5-alpha-Dihydrotestosterone was extracted from plasma (200 1) using benzene:toluene (2:1), with an extraction efficiency of 83.4±6.4 (SD)%. Since further purification of the crude sample extract (i.e., by column chromatography) was not performed, it became necessary to also add extracts from steroid free plasma (i.e., stripped by dextran-coated charcoal) to the standard curve tubes prior to the addition of the different doses of the standard 5-alpha-DHT solutions (3.125 to 1600 pg). This step was necessary since the process of plasma extraction resulted in the presence or production of a plasma contaminant (i.e., stripped serum or plasma blank value) which was consistently higher than the sensitivity of the assay (<50.0 pg/ml), that value being 400 pg/ml [CV of 13.7% and 6.3% for between (n=4) and within (n=8) assay(s), respectively]. Following the drying process (Savant-high speed concentrator), 200 microliters 5-alpha-DHT anti-serum solution were added to each standard or unknown. After brief vortex mixing, 200 microliters of [1,2,3,7-$^3$H] 5-alpha-DHT (~10,000 cpm) was added to each tube and the mixture allowed to incubate overnight at 4° C. The antibody-hormone-bound fraction was separated from the non-bound fraction using a charcoal-dextran suspension. Radioactivity of the bound fraction was measured using a liquid scintillation counter. The percentage bound of the standards was plotted against the log of the hormone concentration to yield a standard curve. Potency estimates of the unknowns were calculated from this standard curve.

Sensitivity of the assay was less than 50.0 pg/ml, while the mean within-assay CV for the low (37.7 pg/ml for plasma stripped and pooled from 3 adult male White Leghorn chickens) and high (265 pg/ml for plasma pooled and not stripped from 3 adult male White Leghorn chickens) plasma pools (n=5) was less than 9.4%. The mean between-assay CV for the low and high plasma pools was less than 12.9% (n=7). A typical standard curve (n=7) using 3.125 to 1600 pg 5-alpha-DHT showed 50 percent inhibition of binding to be achieved with 67.4±8.2 pg/tube (CV=12.2%). Twenty and 80 percent inhibition of binding were achieved respectively with 16.9±2.1 pg/tube (CV=12.6%) and 321.4±31.9 pg/tube (CV=9.9%).

References cited in the Examples:

Carl, L. E., and M. C. Nesheim, 1972. Capon Production. Pages 132–137 in Poultry Production. Lea and Febiger, Philadelphia, Pa.

Johnson, A. L., and V. T. Rendano, 1984. Effects of castration, with and without testosterone replacement, on leg bone integrity in the domestic fowl. *Am. J. Vet. Res.* 45:319–325.

King, D., 1969. Effect of hypophysectomy of young cockerels with particular reference to body growth, liver weight and liver glycogen level. *Gen. Comp. Endocrinol.* 12:242–255.

Quigley, G.D., 1967. Coponizing chickens. Inst. Appl. Agr. Maryland and Animal Husbandry Res. Div., Agr. Serv. U.S. Govt. Printing Office, Washington, D.C.

Saartok, T., E. Dahlberg and J. A. Gustafsson, 1984. Relative binding affinity of anabolic-androgenic steroids: Comparison of the binding to the androgen receptors in skeletal muscle and in prostrate, as well as to sex hormone-binding globulin. *Endocrinology* 114:2100–2106.

Satyaswaroop, P. T., R. J. Zaino and R. Mortel, 1984. Estrogen-like effects of tamoxifen on human endometrial carcinoma transplanted into nude mice. *Cancer Research* 44:4006–4010.

Smith, E. R., D. A. Dammassa and J. M. Davidson, 1977. Hormone administration: Peripheral and intracranial implants; in Meyers R.D. (ed.): Methods in Psychobiology. N.Y., Academic Press Inc., pp. 259–280.

Certain modifications of the methods and compositions of this invention as above described will be suggested to those in the art of growing turkeys and insofar as they come within the spirit of this invention, are intended to be within the scope thereof.

TABLE 1

COMPARISON OF EFFECTS OF TESTOSTERONE AND 5-ALPHA-DIHYDROTESTOSTERONE ON GROWTH IN MALE AND FEMALE (WHITE LEGHORN) CHICKENS.

| Treatment Groups | N | Initial 2-week Body Weight (g) | 6-week Body Weight (g) | Change % | Final 12-week Body Weight (g) | Change % | 12-week Shark-Toe Length (cm) | Change % |
|---|---|---|---|---|---|---|---|---|
| Intact Male Implanted with:[a] | | | | | | | | |
| Cholesterol (1.0-cm) | 10 | 149 ± 4 | 646 ± 22 | — | 1395 ± 56 | — | 17.1 ± 0.24 | — |
| Testosterone (1.0-cm) | 10 | 149 ± 4 | 585 ± 13* | (9.4%) | 1275 ± 27* | (8.6%) | 16.5 ± 0.17* | (3.1%) |
| 5-alpha-DHT (1.0-cm) | 10 | 149 ± 3 | 535 ± 27*** | (17.2%) | 1171 ± 50*** | (16.1%) | 15.9 ± 0.24*** | (7.0%) |
| Intact Female | | | | | | | | |

TABLE 1-continued

COMPARISON OF EFFECTS OF TESTOSTERONE AND 5-ALPHA-DIHYDROTESTOSTERONE ON GROWTH IN MALE AND FEMALE (WHITE LEGHORN) CHICKENS.

| Treatment Groups | N | Initial 2-week Body Weight (g) | 6-week Body Weight (g) | Change % | Final 12-week Body Weight (g) | Change % | 12-week Shark-Toe Length (cm) | Change % |
|---|---|---|---|---|---|---|---|---|
| Implanted with:[a] | | | | | | | | |
| Cholesterol (1.0-cm) | 10 | 148 ± 5 | 587 ± 14 | — | 1124 ± 28 | — | 15.1 ± 0.17 | — |
| Testosterone (1.0-cm) | 10 | 149 ± 4 | 553 ± 11 | (5.8%) | 1067 ± 22* | (5.1%) | 14.7 ± 0.09 | (2.6%) |
| 5-alpha-DHT (1.0-cm) | 10 | 149 ± 4 | 529 ± 12* | (9.9%) | 1051 ± 15* | (6.5%) | 14.6 ± 0.12* | (3.3%) |

[a]Steroid treatments entailed the subcutaneous implantation (between the shoulders) of 1.0-cm length, silastic implants (crystalline steroids at 2, 6 and 10 weeks of age.)
Significantly different from cholesterol-implanted, control (males or females as indicated) birds (*$P < 0.05$; **$P < 0.01$; $P < 0.001$) by ANOVA and LSD.

TABLE II

COMPARISON OF EFFECT OF TESTOSTERONE (3 DOSES) AND 5-ALPHA-DHT (3-DOSES) ON GROWTH IN CASTRATED MALE (WHITE LEGHORN) CHICKENS.

| Treatment Groups | Initial 2-week Body Wt. (g) | 6-week Body Wt. (g) | Change (%) | 12-week Body Wt. (g) | Change (%) | Right Breast Muscle (g) |
|---|---|---|---|---|---|---|
| Castrated Male[a] Implanted with:[b] | | | | | | |
| Cholesterol | 111 ± 5 n = 15 | 513 ± 10 n = 15 | — | 1279 ± 34 n = 15 | — | 64 ± 2 n = 14 |
| Testosterone (0.3-cm) | 111 ± 5 n = 15 | 501 ± 13 n = 15 | — | 1262 ± 35 n = 15 | — | 61 ± 2 n = 14 |
| (0.1-cm) | 111 ± 4 n = 15 | 503 ± 10 n = 15 | — | 1287 ± 25 n = 15 | — | 61 ± 2 n = 14 |
| (3.0-cm) | 111 ± 5 n = 15 | 505 ± 13 n = 15 | — | 1207 ± 25* n = 15 | (5.6%) | 55 ± 2** n = 14 |
| 5-alpha-DHT (0.3-cm) | 111 ± 5 n = 15 | 515 ± 10 n = 15 | — | 1191 ± 26* n = 15 | (6.9%) | 57 ± 2* n = 14 |
| (1.0-cm) | 111 ± 4 n = 15 | 485 ± 12 n = 15 | — | 1140 ± 39** n = 15 | (10.9%) | 51 ± 3*** n = 13 |
| (3.0-cm) | 111 ± 4 n = 15 | 415 ± 15*** n = 15 | (19.1%) | 872 ± 53*** n = 15 | (31%) | 36 ± 3 n = 11 |

| Treatment Groups | Change (%) | Actipose Abdominal (g) | Change (%) | Final 12-week Shark-toe Length (cm) | Change (%) |
|---|---|---|---|---|---|
| Castrated Male[a] Implanted with:[b] | | | | | |
| Cholesterol | — | 24 ± 3 n = 14 | — | 17.0 ± 0.17 n = 14 | — |
| Testosterone (0.3-cm) | — | 16 ± 2** n = 14 | (33.3%) | 17.0 ± 0.16 n = 14 | — |
| (0.1-cm) | — | 15 ± 3** n = 14 | (37.5%) | 16.9 ± 0.14 n = 14 | — |
| (3.0-cm) | (14.1%) | 10 ± 3*** n = 14 | (58.3%) | 16.4 ± 0.16* n = 14 | (3.5%) |
| 5-alpha-DHT (0.3-cm) | (10.9%) | 10 ± 2*** n = 14 | (58.3%) | 16.4 ± 0.10* n = 14 | (3.5%) |
| (1.0-cm) | (15.6%) | 6 ± 1*** n = 14 | (75.0%) | 16.1 ± 0.24** n = 14 | (5.3%) |
| (3.0-cm) | (43.8%) | 0.5 ± 0.2*** n = 11 | (97.9%) | 13.7 ± 0.34*** n = 14 | (19.4%) |

[a]Birds castrated at 2 weeks of age.
[b]Steroid treatments entailed the subcutaneous implantation (between the shoulders) of 0.3-, 1.0-, or 3.0-cm length silastic implants (crystalline steroid) at 2, 6 and 10 weeks of age.
Significantly different from cholesterol-implanted control (castrated males) birds. (*$P < 0.05$; **$P 0.01$; $P < 0.001$) by ANOVA and LSD.

TABLE III

COMPARISON OF EFFECT OF 19-NORTESTOSTERONE (3 DOSES) AND 5-ALPHA-DHT (1-DOSE) ON GROWTH IN CASTRATED MALE (WHITE LEGHORN) CHICKENS.

| Treatment Groups | N | Initial 2-week Body Wt. (g) | Final[c] 6-week Body Wt. (g) | Change (%) | Right Breast Muscle (g) | Change (%) | Abdominal Actipose (g) | Change (%) | Final Shark-toe Length (cm) | Change (%) |
|---|---|---|---|---|---|---|---|---|---|---|
| Castrated Male[a] Implanted with:[b] | | | | | | | | | | |
| Chlolesterol (1.0-cm) | 12 | 89 ± 5 | 462 ± 13 | — | 19.8 ± 0.73 | — | 3.06 ± 0.36 | — | 11.9 ± 0.1 | — |
| 19-Nortestosterone (0.3-cm) | 12 | 87 ± 3 | 384 ± 18*** | (16.9%) | 13.9 ± 1.1*** | (29.8%) | 1.26 ± 0.19*** | (58%) | 10.8 ± 0.13*** | (9.2%) |
| (1.0-cm) | 12 | 87 ± 2 | 351 ± 13*** | (24.0%) | 13.2 ± 0.87*** | (33.3%) | 0.26 ± 0.08*** | (91%) | 10.2 ± 0.12*** | (14.3%) |
| (3.0-cm) | 12 | 87 ± 2 | 349 ± 19*** | (24.5%) | 12.0 ± 0.96*** | (39.4%) | 0.58 ± 0.12*** | (81%) | 9.8 ± 0.17*** | (17.6%) |
| 5-alpha-DHT (1.0-cm) | 12 | 87 ± 2 | 422 ± 10* | (8.6%) | 16.3 ± 0.67** | (17.7%) | 2.05 ± 0.12*** | (33%) | 11.4 ± 0.07** | (4.2%) |

[a]Birds castrated at 2 weeks of age.
[b]Steroid treatments entailed the subcutaneous implantation (between the shoulders) of 0.3-, 1.0- or 3.0-cm length silastic implants (crystalline steroid) at 2 weeks of age.
[c]Final body weight = body weight − (comb + wattle weight) at 6 weeks of age.
Significantly different from cholesterol-implanted control (castrated males) birds (*$P < 0.05$; $P\ 0.01$; *$P < 0.001$) by ANOVA and LSD.

TABLE IV

COMPARISON OF EFFECT OF TESTOSTERONE (2 DOSES), 5-ALPHA-DHT (2 DOSES) AND 19-NORTESTOSTERONE (2 DOSES) ON GROWTH IN FEMALE (LARGE WHITE NICHOLAS) TURKEYS.

| Treatment Groups | N | Initial 6-Week Body Weight (g) | Final 9-Week Body Weight (g) | (%) | Right Breast Muscle (g) | (%) | Abdominal Adipose (g) |
|---|---|---|---|---|---|---|---|
| Intact Female Implanted With: | | | | | | | |
| Placebo | 11 | 1842 ± 66 | 4010 ± 108 | — | 390 ± 15 | — | 29.7 ± 3.9 |
| Testosterone (5-mg) | 11 | 1822 ± 47 | 4096 ± 65 | — | 430 ± 15 | — | 20.2 ± 1.6* |
| (50-mg) | 11 | 1819 ± 42 | 4320 ± 69* | (7.7%) | 477 ± 17** | (22.3%) | 22.8 ± 2.5* |
| 5-alpha-DHT (5-mg) | 11 | 1823 ± 46 | 4073 ± 72 | — | 415 ± 7 | — | 21.4 ± 2.2* |
| (50-mg) | 11 | 1815 ± 39 | 4365 ± 84** | (8.9%) | 487 ± 13** | (24.9%) | 20.2 ± 3.3* |
| 19-Nortestosterone (5-mg) | 11 | 1840 ± 60 | 4115 ± 122 | — | 439 ± 15* | (12.6%) | 22.8 ± 2.14* |
| (50-mg) | 11 8 | 1819 ± 44 | 4476 ± 94*** | (11.6%) | 493 ± 17*** | (26.4%) | 18.7 ± 2.04** |

| Treatment Groups | (%) | Feed/Grain[c] Ratio | (%) | Final 9-Week Shark-Toe Length (cm) | (%) | Average Daily Gain (g) | (%) |
|---|---|---|---|---|---|---|---|
| Intact Female Implanted With: | | | | | | | |
| Placebo | — | 2.11 ± 0.02 (n = 4) | — | 18.5 ± 0.22 | — | 103 ± 2 | — |
| Testosterone (5-mg) | (32%) | 2.01 ± 0.05 (n = 4) | — | 18.9 ± 0.16 | — | 108 ± 2 | — |
| (50-mg) | (23%) | 1.91 ± 0.04** (n = 4) | (9.5%) | 18.6 ± 0.13 | — | 119 ± 3*** | (15.5%) |
| 5-alpha-DHT (5-mg) | (28%) | 2.03 ± 0.03 (n = 4) | — | 18.6 ± 0.21 | — | 106 ± 2 | — |
| (50-mg) | (32%) | 1.82 ± 0.03*** (n = 4) | (13.7%) | 18.79 ± 0.25 | — | 121 ± 3*** | (17.5%) |
| 19-Nortestosterone (5-mg) | (23%) | 1.92 ± 0.04 (n = 4) | (9.0%) | 18.87 ± 0.25 | — | 108 ± 3 | — |
| (50-mg) | (37%) | 1.76 ± 0.07*** | (16.6%) | 18.31 ± 0.24 | — | 127 ± 3*** | (23.3%) |

[a]5- or 50-mg slow release pellets (Innovative Research) administered subcutaneiously at 6 weeks of age.
[b]Data for Feed to Gain Ratio is computed for the period 6 through 9 weeks of age. Experimental units are floor pens (n = 4) of 3 to 4 turkeys values are means and SEM of the pen averages.
Significantly different from placebo-implanted control (intact females) birds (*$P < 0.05$; $P < 0.01$; *$P < 0.001$) by ANOVA and LSD.

TABLE V

COMPARISON OF EFFECT OF TESTOSTERONE, 5-ALPHA-DHT AND 19-NORTESTOSTERONE ON GROWTH IN INTACT AND CASTRATED MALE (LARGE WHITE NICHOLAS) TURKEYS.

| Treatment Groups | N | Initial 7-Week 6-Week Body Weight (g) | Final 10-Week 9-Week Body Weight (g) | (%) | Right Breast Muscle (g) | (%) | Abdominal Actipose (g) |
|---|---|---|---|---|---|---|---|
| Intact Male Implanted With: | | | | | | | |
| Placebo | 8 | 2652 ± 54 | 4909 ± 86 | — | 429 ± 10 | — | 16.7 ± 2.97 |
| Testosterone (50-mg)$^a$ | 8 | 1647 ± 52 | 5100 ± 82 | — | 450 ± 10 | — | 11.61 ± 1.37 |
| (5-cm)$^b$ | 8 | 2645 ± 42 | 5055 ± 61 | — | 457 ± 20 | — | 13.2 ± 3.57 |
| 5-alpha-DHT (50-mg)$^a$ | 8 | 2673 ± 50 | 5202 ± 44** | (6.0%) | 460 ± 10* | (7.2%) | 9.53 ± 1.12 |
| (5-cm)$^b$ | 8 | 2624 ± 34 | 4985 ± 60 | — | 465 ± 17* | (8.4%) | 12.2 ± 1.44 |
| 19-Nortestosterone (50-mg)$^a$ | 8 | 2638 ± 42 | 5416 ± 136*** | (10.3%) | 529 ± 22*** | (23.3%) | 6.74 ± 1.57*** |
| (5-cm)$^b$ | 8 | 2650 ± 36 | 5410 ± 73*** | (10.2%) | 513 ± 15*** | (12.6%) | 7.88 ± 2.10*** |
| Castrated Male$^d$ Implanted With: | | | | | | | |
| Placebo | 9 | 1430 ± 20 | 3441 ± 56 | — | 264 ± 7 | — | 12.47 ± 1.80 |
| 19-Nortestosterone (5-cm)$^a$ | 9 | 1427 ± 18 | 3643 ± 64** | (5.9%) | 303 ± 13*** | (14.8%) | 4.92 ± 0.91*** |

| Treatment Groups | (%) | Feed/Grain$^c$ Ratio | Feed Efficiency (g) | Final 10-Week 9-Week Shark-Toe Length (cm) | (%) | Average Daily Gain (g) | (%) |
|---|---|---|---|---|---|---|---|
| Intact Male Implanted With: | | | | | | | |
| Placebo | — | 2.54 ± 0.061 (n = 4) | — | 23.9 ± 0.22 | — | 109 ± 2 | — |
| Testosterone (50-mg)$^a$ | — | 2.37 ± 0.086 (n = 4) | — | 23.6 ± 0.19 | — | 116 ± 4 | — |
| (5-cm)$^b$ | — | 2.39 ± 0.008 (n = 4) | — | 24.2 ± 0.18 | — | 115 ± 2 | — |
| 5-alpha-DHT (50-mg)$^a$ | — | 2.33 ± 0.079 (n = 4) | — | 24.3 ± 0.28 | — | 120 ± 3* | (10.1%) |
| (5-cm)$^b$ | — | 2.30 ± 0.120* (n = 4) | (9.4%) | 24.4 ± 0.15 | — | 113 ± 3 | — |
| 19-Nortestosterone (50-mg)$^a$ | (59.6%) | 1.99 ± 0.091*** (n = 4) | (21.6%) | 23.3 ± 0.22 | — | 132 ± 6*** | (21.1%) |
| (5-cm)$^b$ | (52.8%) | 1.94 ± 0.041*** | (23.6%) | 23.5 ± 0.15 | — | 131 ± 3*** | (20.2%) |
| Castrated Male$^d$ Implanted With: | | | | | | | |
| Placebo | — | 2.23 ± 0.06 | — | 21.8 ± 0.13 | — | 91 ± 3 | — |
| 19-Nortestosterone (5-cm)$^a$ | (65.6%) | 1.85 ± 0.05*** | (16.6%) | 21.44 ± 0.18 | — | 106 ± 3*** | (16.5%) |

What is claimed is:

1. A method for increasing the rate of growth or feed efficiency of turkeys, which comprises administering to said turkeys a growth promoting mount of 5-alpha-dihydrotestostetone in the range of at least 5 mg to at least about 50 mg as a bioacceptable and biocompatible implant which releases said [19-nortostosterone] 5-alpha-dihydrotestosterone to provide said increasing the rate of growth or feed efficiency of turkeys, biocompatible alkanoic acid ester derivatives thereof which are effective in carrying out growth promotion in turkeys, and combinations thereof.

2. A method of claim 1 wherein the implant is a subcutaneously inserted implant.

3. A method of claim 2 wherein the implant is a polysiloxane capsule containing 5-alpha-dihydrotestosterone.

4. A method of claim 2 wherein the implant contains an effective amount of 5-alpha-dihydrotestosterone of at least about 20 mg.

5. A method of claim 3 wherein the implant contains an effective amount of 5-alpha-dihydrotestosterone of at least about 50 mg.

6. A method of claim 1 wherein the implant is a polymer mass pellet.

7. A method of claim 6 wherein the polymer mass pellet has 5-alpha-dihydrotestosterone encapsulated in an insoluble polymer mass which permits release of 5-alpha-dihydrotestosterone by diffusion.

8. A method of claim 6 wherein the polymer mass pellet has dispersed therein 5-alpha-dihydrotestosterone, said polymer mass by slow dissolution provides effective administration of 5-alpha-dihydrotestosterone.

* * * * *

UNITED STATES PATENT AND TRADEMARK OFFICE
CERTIFICATE OF CORRECTION

PATENT NO. : 5,407,681
DATED : April 18, 1995
INVENTOR(S) : Colin G. Scanes et al

It is certified that error appears in the above-indentified patent and that said Letters Patent is hereby corrected as shown below:

Column 17, line 56, claim 1, the text should read:

"implant which releases said 5-alpha-dihydrotestosterone to provide said increasing..."

Signed and Sealed this

Seventeenth Day of October, 1995

Attest:

BRUCE LEHMAN

*Attesting Officer*    *Commissioner of Patents and Trademarks*